United States Patent [19]

Lin et al.

[11] Patent Number: 5,550,303

[45] Date of Patent: Aug. 27, 1996

[54] HIGH EFFICIENCY OLEFIN DISPLACEMENT PROCESS

[75] Inventors: Ronny W. Lin; Robert H. Allen; Andrew D. Overstreet, all of Baton Rouge, La.

[73] Assignee: Amoco Corporation, Chicago, Ill.

[21] Appl. No.: 459,080

[22] Filed: Jun. 2, 1995

[51] Int. Cl.$^6$ .................................................. C07F 5/06
[52] U.S. Cl. ........................... 585/328; 585/637; 556/190
[58] Field of Search .................................. 585/522, 328, 585/637; 556/190

[56] References Cited

U.S. PATENT DOCUMENTS

| | | | |
|---|---|---|---|
| 2,962,513 | 11/1960 | Meiners et al. | 260/448 |
| 3,389,161 | 6/1968 | Kottong et al. | 260/448 |
| 4,314,090 | 2/1982 | Shewbart et al. | 585/328 |
| 4,380,684 | 4/1983 | Fowler et al. | 585/328 |
| 4,918,254 | 4/1990 | Diefenbach et al. | 585/328 |
| 5,124,465 | 6/1992 | Allen et al. | 556/190 |
| 5,191,145 | 3/1993 | Allen et al. | 585/664 |
| 5,274,153 | 12/1993 | Allen et al. | 556/190 |

*Primary Examiner*—Glenn A. Caldarola
*Attorney, Agent, or Firm*—Stephen L. Hensley

[57] ABSTRACT

Olefin is formed by displacing alkyl groups of aluminum trialkyl by contacting ethylene with the aluminum trialkyl in an ethylene:aluminum trialkyl mol ratio in the range of 2–8:1 at about 0°–70° C. and at atmospheric up to about 1000 psia pressure, for a reaction time of about 0.5 to about 60 minutes in the presence of a displacement enhancing amount of a nickel- or cobalt-containing displacement catalyst. Despite the fact that the displacement reaction is an equilibrium reaction, the process does not use, as did the prior art, large excesses of ethylene to shift the equilibrium to favor displacement. Consequently, the volumes of ethylene used in the processing are reduced very substantially and yet yields of the desired displaced alpha olefin remain favorable. Additionally, inasmuch as the process is conducted at relatively low temperatures and does not require high pressures, the energy requirements for the process are modest—far less, for example, than required in thermal displacement operations.

10 Claims, No Drawings

5,550,303

1

HIGH EFFICIENCY OLEFIN DISPLACEMENT PROCESS

TECHNICAL FIELD

This invention relates to the production of alpha olefins from aluminum alkyls by a novel, highly efficient catalytic displacement process. As used herein the term "olefin" refers to monoolefin, that is, an aliphatic hydrocarbon having a single ethylenic type double bond in the molecule.

BACKGROUND

It has long been known that alpha olefins can be produced from aluminum alkyls by displacement of the alkyls as alpha olefins by reaction of aluminum alkyl with a different olefin under suitable reaction conditions. One type of process involves thermal displacement wherein the displacing olefin and aluminum alkyl are reacted at 280°–320° C. to effect the displacement. Such processes require raped cooling to about 120° C. to minimize isomerization and other undesired side reactions. A process of this type is described in Davis et al. U.S. Pat. No. 3,391,219.

The other type of displacement processes involves use of a catalyst to facilitate the displacement reaction. One such process is described in Diefenbach et al. U.S. Pat. No. 4,918,254. In that process the displacement is catalyzed by use of a nickel catalyst in a reaction wherein preferably at least a 200 percent excess (i.e., 9 moles of olefin per mole of $AlR_3$) and more preferably at least a 500 percent excess of displacing olefin is used over the stoichiometric amount required to replace all alkyl groups of the aluminum alkyl. As the patentees indicate, such large excesses of displacing olefin are used because the displacement reaction is an equilibrium reaction. Thus use of large excesses is intended to shift the equilibrium so that the alkyl substitution in the second trialkyl aluminum will more closely approach the distribution of the displacing olefin.

THE INVENTION

This invention involves the surprising discovery that when ethylene is used as the displacing olefin, such large excesses relative to the aluminum alkyl reactant are not required. More particularly, it has been found that the equilibrium constant of a suitably catalyzed displacement reaction in which the displacing olefin is ethylene is highly favorable toward displacement, provided relatively low displacement reaction temperatures are used. Accordingly at least two major benefits arise by virtue of this invention. First, the volumes of ethylene used in the processing are reduced very substantially and yet yields of the desired displaced alpha olefin remain favorable. Secondly, inasmuch as the process is conducted at relatively low temperatures and does not require high pressures, the energy requirements for the process are modest—far less, for example, than required in thermal displacement operations.

In accordance with one embodiment, this invention provides a process for displacing olefin having from 3 to about 40 carbon atoms per molecule from an aluminum trialkyl having 3 to about 40 carbon atoms per alkyl group which comprises contacting ethylene with said aluminum trialkyl in an ethylene:aluminum trialkyl mol ratio in the range of 2–8:1 at a temperature in the range of about 1 to about 70° C., a pressure in the range of from about atmospheric pressure up to about 1000 psia, and for a reaction time in the range of about 0.5 to about 60 minutes in the presence of a displacement enhancing amount of a nickel- or cobalt- containing displacement catalyst. The preferred ratio of ethylene to aluminum trialkyl in the displacement reaction zone is from 4 to 8 mols of ethylene per mol of aluminum trialkyl.

Preferred embodiments of this invention involve use of displacement temperatures in the range of about 20 to about 50° C. In other preferred embodiments the pressures in the displacement reactor are in the range of about 30 to about 500 psia. It is especially preferred to employ the combination of temperatures in the range of about 20 to about 50° C. and pressures in the range of about 30 to about 500 psia.

Another preferred embodiment of this invention comprises conducting the above catalytic displacement reaction at with conditions controlled such that the ratio of the temperature in degrees centigrade to contact time in minutes is not greater than 40:1.

These and other embodiments and features of this invention will become still further apparent from the ensuing description and appended claims.

Aluminum Trialkyl

The process of this invention enables formation of alpha-olefins by displacement from aluminum trialkyl of alkyl groups which typically have in the range of 3 to about 40 carbon atoms each. In preferred operations the initial aluminum trialkyl has in the range of 4 to about 20 carbon atoms per alkyl group whereby alpha-olefins of 4 to about 20 atoms are produced for recovery or use in other process operations.

The aluminum trialkyl from which the alpha-olefins are released through displacement by ethylene are compounds in which the alkyl groups are predominantly if not entirely primary alkyl groups. Usually the alkyl groups are linear in structure with little, if any, branching along the chain. The aluminum trialkyl reactant can be a single compound, but typically will be a mixture of two or more aluminum trialkyls in which the alkyl groups have different chain lengths. Such compounds can be produced by known process technology such as catalytic or stoichiometric chain growth reactions. As noted above, the alkyl group(s) present in the aluminum trialkyl used in the process of this invention will normally have in the range of 4 to about 40 carbon atoms each. A few examples of such compounds are tributylaluminum, tripentylaluminum, trihexylaluminum, triheptylaluminum, trioctylaluminum, tri(decyl)aluminum, tri(dodecyl)aluminum, tri(tetradecyl)aluminum and the higher homologs of such aluminum trialkyls, and mixtures of such compounds. Often the aluminum trialkyls used in the process will be a mixture in which the alkyl groups differ in chain lengths by multiples of two and have even numbers of carbon atoms, such as mixtures of aluminum trialkyls in which the alkyls contain, say, 6, 8, 10, 12, 14 and 16 carbon atoms.

If the aluminum trialkyl contains dialkylaluminum hydride in more than trace amounts, the alkyl aluminum mixture should be pretreated with an alpha-olefin, preferably ethylene, to convert the aluminum-hydrogen bonds to alkyl-aluminum bonds, as the presence of alkylaluminum hydride is harmful to the displacement catalyst.

Displacement Catalyst

The catalysts which are included in the displacement reaction mixture are compounds or complexes of nickel or cobalt. Mixtures of suitable nickel and cobalt compounds can be used, if desired. Preferably the nickel or cobalt compounds are sufficiently soluble in organic media, such as hydrocarbons, so that they perform as homogeneous catalysts. However it is possible, though less preferable, to employ heterogeneous nickel and/or cobalt catalysts such as colloidal forms of the metals themselves or relatively hydrocarbon-insoluble inorganic compounds thereof, which may be fixed on suitable supports. These displacement catalyst materials are exemplified by such nickel compounds as nickel carboxylates such as nickel naphthenate and nickel stearate, nickel bis(acetylacetonate), nickelocene, bis(1,5-cyclooctadiene)nickel, nickel octylacetoacetate complex, nickel ethylenediamine tetraacetic acid complex, and similar nickel compounds or complexes. Examples of suitable cobalt compounds include cobalt carboxylates such as cobalt naphthenate and cobalt oleate, cobalt bis(acetylacetonate), cobaltacene, cobalt octylacetoacetate complex, cobalt ethylenediamine tetraacetic acid complex and like substances.

Amounts of the displacement catalyst typically fall in the range equivalent to about 1 to about 100 parts by weight of nickel and/or cobalt per million parts of reaction mixture. However, amounts outside of this range can be used whenever deemed necessary or desirable under any given set of circumstances under consideration.

At any convenient stage after completion of the displacement reaction, the displaced olefin product and unreacted ethylene are recovered and separated from each other, for example by flashing off the ethylene or by use of distillation procedures.

For further details concerning nickel catalyzed displacements one may refer, for example, to U.S. Pat. No. 4,918,254, the entire disclosure of which is incorporated herein by reference. Use of nickel and cobalt displacement catalysts is referred to in U.S. Pat. No. 5,124,465, the entire disclosure of which is also incorporated herein by reference. Other suitable displacement catalysts have been reported in the literature.

Reaction Diluent

It is preferred to conduct the reaction in bulk, i.e., without use of an inert diluent. But an inert hydrocarbon diluent such as a paraffinic, cycloparaffinic or aromatic hydrocarbon or mixture of two or more of such hydrocarbons can be used for the reaction, if desired. A few illustrative examples include one or more isomeric forms of heptane, octane, nonane or decane; cycloparaffins such as cyclopentane, methylcyclopentane, cyclohexane, or cycloheptane; and aromatics such as toluene, one or more xylene isomers, tetrahydronaphthalene, and commercially available mixtures of suitable boiling points such as gasoline fractions, petroleum ethers, mixed alkanes, mixed cycloalkanes and mixed mononuclear aromatic hydrocarbons.

Subsequent Processing

It is desirable, especially when the displacement catalyst used is a nickel catalyst, to deactivate the catalyst by use of a deactivating amount of a catalyst deactivator, preferably a hydrocarbon-soluble lead (II) compound. The use of a lead compound to deactivate the nickel or cobalt displacement catalyst precludes the possibility of undesired side reactions such as isomerization, oligomerization or polymerization from occurring. Suitable lead compounds include lead carboxylate salts, lead chelates or complexes, and other lead (II) compounds. Preferred materials include lead acetate, lead hexanoate, lead octanoate, lead 2-ethylhexanoate, lead naphthenate, and similar lead carboxylates; and lead chelates such as lead acetylacetonate and lead octylacetoacetate. The amount used should be an amount sufficient to deactivate the nickel or cobalt catalyst. Typically the amount will be sufficient to provide an Pb:Ni or Pb:Co atom ratio in the range of about 0.5:1 to about 5:1. Excess soluble lead in the product mixture has been found not to adversely affect subsequent reactions in which the trialkyl aluminum reaction product (which is highly enriched in triethylaluminum) may be used, and preferably is used, such as a chain growth reaction with ethylene. Thus there appears to be no critical upper limit on lead concentration.

The catalyst deactivation is performed at any suitable temperature within the range of about 0° to about 130° C., and preferably within the range of about 20° to about 110° C. It is desirable to agitate the mixture to ensure good contact between the lead catalyst deactivator and the nickel or cobalt catalyst.

It is also preferred to conduct a thermal agglomeration/conglomeration of the solids produced in the catalyst deactivation step. This operation typically involves maintaining the stirred or otherwise agitated reaction mixture at a temperature in the range of about 90° to about 150° C. for a period of at least about 1 minute. Preferably, a major portion of the agglomeration/conglomeration is performed at one or more temperatures in the range of about 100° to about 120° C.

The agglomerated solids are then removed from the reaction mixture by any suitable procedure such as filtration, decantation, or centrifugation. Normally filtration is employed. An advantage resulting from the use of an agglomeration/conglomeration stage is that the solids are readily separated in the filtration operation which can thus be conducted rather rapidly even on a large scale.

After separating the agglomerated/conglomerated solids from the trialkylaluminum product (which is usually well over 90% triethylaluminum) can be subjected to further processing as desired, such as chain growth with ethylene. For this purpose, the trialkylaluminum product is treated with excess ethylene at a pressure which typically falls in the range of about 1000 to about 5000, more preferably about 2000 to about 3500 psig, and reaction zone temperatures of from about 100° to about 250 C. and preferably about 120° to about 160° C. If desired, a hydrocarbon diluent such as a paraffinic hydrocarbon (e.g. heptane) can be used in the chain growth reaction.

Residence times for a chain growth reaction generally fall in the range of about 10 to about 120 minutes, with the longer times being used when longer chain end products are desired. In most cases, residence times in the range of about 30 to about 90 minutes will suffice to produce desirable second alkyl aluminum products.

Equilibrium Constants

Using displacement of propylene from tripropylaluminum by ethylene as an example, the equilibrium constant ($K_{eq}$) is defined by the expression:

$$K_{eq}=[>Al-C_2][C_3^=]/[>Al-C_3][C_2^=]=[C_2°][C_3^=]/[C_3°][C_2^=]$$

In a series of six displacement operations in which propylene was displaced from tripropylaluminum by ethylene at atmospheric pressure using 20 ppm of Ni(II) as displacement catalyst and in which samples were immediately hydrolyzed with cold hydrochloric acid to convert >Al-$C_2$ and >Al-$C_3$ to $C_2°$ to $C_3°$, and $C_3°$, respectively, for gas chromatography analysis, the equilibrium constants were found to be in the range of 140 to 250 at 18°–24 C.

Another approach for determining the equilibrium constants involved reacting tri-n-octylaluminum and ethylene in a pressurized NMR tube for in-situ $C^{m13}$ and $H^1$ NMR analyses. Use of this technique gave $K_{eq}$ in the range of about 310–350 for 23° C. and of about 220–240 for 50° C. The equilibrium constant ($K_{eq}$) Of the displacement of a trialkyl aluminum with ethylene at these low temperatures is much higher than the equilibrium constant of about 15 for thermal displacements of aluminum alkyls by ethylene typically conducted at temperatures of about 300° C. and pressures of about 200 psia with about 30 mols of ethylene per mol of aluminum alkyl.

In addition, it was found that catalytic displacement using ethylene pursuant to this invention has much more favorable equilibrium constants as compared to catalytic displacements conducted under the same conditions but using olefins other than ethylene as the displacing olefin, especially at a low reaction temperature.

To further illustrate the practice and advantages of this invention, the following non-limiting example is set forth.

EXAMPLE

In a dry box, 1.5 g of tri-n-propylaluminum (TNPA; free of hydrides) and 16.5 g of dry heptane were charged into a 50 cc flask which was then set up under a $N_2$ pad. A flow of ethylene gas was initiated so that it bubbled into the solution at ambient temperature. After 5-minute stirring, 60 microliters of a catalyst solution (0.0056 g Ni(II) per cc of heptane) were fed with a syringe over a period of approximately 5 seconds. After another 5 minutes, ethylene feed was terminated to allow the reaction to reach its equilibrium. Samples were taken at 23° C., with a cooled Gastight syringe, at 10 and 30 minutes after the ethylene feed was turned off. Each sample was immediately injected to a septum-capped vial containing hydrochloric acid and heptane for hydrolysis at 0°–5° C., followed by immediately injecting the resultant organic solution into a gas chromatograph equipped with a flame-detector.

| Sample | GC area % | | | | Estimated |
|---|---|---|---|---|---|
| # | Ethylene | Ethane | Propylene | Propane | $K_{eq}$ |
| 1 | 0.712 | 35.56 | 52.14 | 11.36 | 229 |
| 2 | 0.522 | 26.13 | 38.84 | 8.10 | 240 |

The estimated conversion of TNPA (in sample #2) was 82.7% with an ethylene/TNPA mole ratio of ~2.56:1 (~85.2% of stoichiometric ethylene).

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

We claim:

1. A process for displacing olefin having 3 to 40 carbon atoms per molecule from an aluminum trialkyl having 3 to 40 carbon atoms per alkyl group which comprises contacting ethylene with said aluminum trialkyl in an ethylene:aluminum trialkyl mol ratio in the range of 2–8:1 at a temperature in the range of about 1 to about 70° C., a pressure in the range of from about atmospheric pressure up to about 1000 psia, and for a reaction time in the range of about 0.5 to about 60 minutes in the presence of a displacement enhancing amount of a nickel- or cobalt-containing displacement catalyst.

2. A process according to claim 1 wherein the temperature is in the range of about 20 to about 50° C.

3. A process according to claim 1 wherein the pressure is in the range of about 30 to about 500 psia.

4. A process according to claim 1 wherein the ratio of the temperature in degrees centigrade to contact time in minutes is not greater than 40:1.

5. A process according to claim 1 wherein the temperature is in the range of about 20 to about 50° C., wherein the pressure is in the range of about 30 to about 500 psia and wherein the ratio of the temperature in degrees centigrade to contact time in minutes is not greater than 40:1.

6. A process according to claim 1 wherein the ratio of ethylene to said aluminum trialkyl is in the range of 4 to 8 mols of ethylene per mol of said aluminum trialkyl.

7. A process according to claim 6 wherein the temperature is in the range of about 20 to about 50° C., wherein the pressure is in the range of about 30 to about 500 psia and wherein the ratio of the temperature in degrees centigrade to contact time in minutes is not greater than 40:1.

8. A process according to claim 1 wherein after completion of the displacement reaction the displacement catalyst is deactivated by addition thereto of a displacement catalyst deactivating amount of a lead catalyst deactivator, agglomerating/conglomerating the resultant solids, and separating the agglomerated/conglomerated solids.

9. The process of claim 8 wherein said catalyst deactivator is a hydrocarbon-soluble lead (II) compound.

10. The process of claim 8 wherein the trialkylaluminum product formed in the displacement reaction is subjected to a chain growth reaction with ethylene.

\* \* \* \* \*